(12) United States Patent
Lalonde et al.

(10) Patent No.: US 6,383,180 B1
(45) Date of Patent: May 7, 2002

(54) CLOSED LOOP CATHETER COOLANT SYSTEM

(75) Inventors: Jean-Pierre Lalonde, Verdun; Marwan Abboud, Pierrefonds, both of (CA)

(73) Assignee: CryoCath Technologies Inc., Quebic (CA)

( * ) Notice: Subject to any disclaimer, the term of this patent is extended or adjusted under 35 U.S.C. 154(b) by 0 days.

(21) Appl. No.: 09/489,646

(22) Filed: Jan. 24, 2000

Related U.S. Application Data

(60) Provisional application No. 60/117,175, filed on Jan. 25, 1999.

(51) Int. Cl.[7] .............................................. A61B 18/18
(52) U.S. Cl. ....................................................... 606/22
(58) Field of Search ........................... 606/20–26; 62/6, 62/293, 51.2

(56) References Cited

U.S. PATENT DOCUMENTS

| | | | | |
|---|---|---|---|---|
| 6,051,019 A | * | 4/2000 | Dobak, III | 606/23 |
| 6,190,378 B1 | * | 2/2001 | Jarvinen | 606/21 |

FOREIGN PATENT DOCUMENTS

| | | |
|---|---|---|
| WO | 99/56639 | 11/1999 |
| WO | 99/56640 | 11/1999 |
| WO | 99/56641 | 11/1999 |
| WO | 00/35362 | 6/2000 |

\* cited by examiner

Primary Examiner—Linda C. M. Dvorak
Assistant Examiner—David M. Ruddy
(74) Attorney, Agent, or Firm—Christopher, Weisberg & Crush, P.A.

(57) ABSTRACT

A coolant system for a cryoablation or treatment probe such as a mapping or ablation catheter, or a treatment wand, includes a compressor and condenser having a low pressure inlet side and a high pressure outlet side, wherein the outlet side passes through a heat exchanger and is cooled by the inlet side and conditioned for injection to a catheter inlet. A vacuum return system connectable to the catheter outlet draws thermally expended coolant from the catheter and returns it to the low pressure inlet side. A motorized pressure regulator between the heat exchanger and the catheter inlet determines the pressure of coolant passing into the catheter and thus regulates the cooling rate for a selected mapping or ablation regimen. The low pressure compressor inlet supply preferentially conditions the pressurized coolant to ambient temperature or lower before injection into the catheter, allowing the coolant to travel through the body at ambient before expansion in the tip. In a preferred embodiment, a coolant reservoir feeds into the low pressure inlet side and receives a return flow of excess fluid from a branch off the outlet side of the compressor. The vacuum return assures that coolant does not leak into the blood stream, and preferably various check valves and bypass valves operate in the event of pressure buildup to return fluid to either the inlet or supply from different points along the loop. The coolant mixture preferably has a boiling point of approximately −60° Fahrenheit at about 1–2 bar, and may be compressed to several hundred psi. The entire system is amenable to microprocessor control for providing ablation cooling cycles to operate the catheter tip in accordance with a selected protocol, and for effecting system functions such as recharging and venting of the supply, and shutting down during nonuse or upon occurrence of a fault condition.

6 Claims, 4 Drawing Sheets

CLOSED LOOP CATHETER COOLANT SYSTEM

CROSS-REFERENCE TO RELATED APPLICATIONS

This application claims priority from U.S. Provisional Application No. 60/117,175, filed on Jan. 25, 1999.

STATEMENT REGARDING FEDERALLY SPONSORED RESEARCH

Not Applicable.

BACKGROUND OF THE INVENTION

The present invention relates to a coolant system for a catheter or treatment wand used for cryotreatment of tissue. In particular, the coolant system is of the type which connects to a catheter and pumps coolant through the catheter to chill the tip of the catheter for stunning or ablating tissue, such as cardiac wall tissue, for mapping or treatment purposes. The invention also contemplates ablation systems for non-cardiac tissue, employing, for example, a hand-held treatment wand rather than a catheter delivery system. For purposes of illustration herein, the discussion will be directed primarily to endovascular ablation catheters of the type available for treating cardiac arrhythmias.

A number of cooled catheter systems have been developed for treating tissue in a cardiac setting, either to cool the tissue sufficiently to stun it and allow cold mapping of the heart and/or confirmation of catheter position with respect to localized tissue lesions, or to apply a more severe level of cold to ablate tissue at the site of the catheter ending. In general, the range of treatments which may be effected by a cryocatheter is comparable to the range of applications for RF or thermal ablation catheters, and in particular, these instruments may be configured to achieve either small localized ball shape lesions at the tip of the catheter, or one or more elongated linear lesions extending a length of several centimeters or more along the tip. The latter form of lesion is commonly used to achieve conduction block across a region of the cardiac wall so as to sever a re-entrant pathway, preventing conduction across the region, in order change the cardiac signal path topology, for example, to eliminate a re-entrant pathway responsible for atrial fibrillation or a tachycardia.

In general, when used for endovascular access to treat the cardiac wall, catheters of this type, in common with the corresponding earlier-developed radio frequency or electrothermal ablation catheter, must meet fairly demanding limitations regarding their size, flexibility, and the factors of strength, electrical conductivity and the like which affect their safety and may give rise to failure modes in use. These constraints generally require that the catheter be no larger than several millimeters in diameter so as to pass through the vascular system of the patient to the heart. Thus, any electrodes (in the case of mapping or RF/electrothermal ablation catheters), and any coolant passages (in the case of cryocatheters) must fit within a catheter body of small size.

A number of different fluids have been used for the coolant component of prior art cryotreatment catheters. Among these may be mentioned a cool liquid such as a concentrated saline solution or other liquid of suitably low freezing point and viscosity, and of suitably high thermal conductivity and heat capacity, or a liquified gas such as liquid nitrogen. In all such constructions, the coolant must circulate through the catheter, thus necessitating multiple passages leading to the cooling area of the tip from the catheter handle.

Furthermore, conditions of patient safety must be considered, raising numerous problems or design constraints for each particular system. Thus for example, a high pressure may be required to circulate sufficient coolant through the catheter body to its tip and back, and the overall design of a catheter must be such that fracture of the catheter wall or leakage of the coolant either does not occur, or if it occurs, is harmless. Further, for an endovascular catheter construction, the presence of the coolant and circulation system should not substantially impair the flexibility or maneuverability of the catheter tip and body.

To some extent these considerations have been addressed by using a phase change material as the cryogenic fluid, and arranging the catheter such that the phase change, e.g., from a liquid to a gas, occurs in the treatment portion of the catheter tip.

Another possible approach is to employ a pressurized gas, and configure the catheter for cooling by expansion of the gas in the tip structure. However, owing to the small size that such a catheter is required to assume for vascular insertion, or the awkwardness of handling a cryogenic treatment probe generally, the design of a safe and effective coolant circulation system which nonetheless dependably provides sufficient cooling capacity at a remote tip remains a difficult goal.

Among other common problems to be addressed while providing adequate thermal capacity, may be noted the leakage problem mentioned above, the problem of effectively preventing the catheter as a whole from being excessively cold or damaging tissue away from the intended site, and the problem of conduit or valve blockage owing for example to ice particles and the like.

Accordingly, it would be desirable to provide a coolant system which conveniently attaches to a cryocatheter.

It would also be desirable to provide a closed loop coolant system which injects and retrieves the coolant from the catheter to allow continuous operation without leakage into the environment or other loss of coolant.

It would further be desirable to provide a closed loop treatment system which precisely controls ablation and treatment regimens by conditioning the coolant supply side of a closed loop.

SUMMARY OF THE INVENTION

These and other desirable features are obtained in a coolant system for a cryoablation or treatment probe such as a mapping or ablation catheter, or a treatment wand, which includes a compressor and condenser having a low pressure inlet side and a high pressure outlet side, wherein the outlet side passes through a heat exchanger to be cooled by the inlet side and conditioned for injection to a catheter inlet, and further comprising a vacuum return system connectable to the catheter outlet to cause thermally expended coolant from the catheter to flow through the vacuum system and be returned to the low pressure inlet side. A motorized pressure regulator between the heat exchanger and the catheter inlet determines the flow rate of coolant passing into the catheter and thus regulates the cooling power for a selected mapping or ablation regimen.

Preferably, the low pressure inlet operates at relatively low temperatures so that heat exchange conditions the relatively warm pressurized coolant to ambient temperature or colder before injection into the catheter, allowing the coolant to travel at near ambient temperature to the tip before expansion and cooling to perform mapping or ablation as appropriate. In a preferred embodiment, a coolant reservoir feeds into the low pressure inlet side and receives a return flow of excess fluid from a branch off the outlet side of the compressor. The vacuum return assures that coolant does not leak into the blood stream, and preferably various check valves and bypass valves operate in the event of pressure buildup to return fluid to the inlet or supply loops. The coolant mixture preferably has a boiling point of approximately −60° Fahrenheit at about one atmosphere, and may be compressed to several hundred psi. The entire system is amenable to microprocessor control for providing ablation cooling cycles to operate the catheter tip in accordance with a selected protocol, and for effecting system functions such as recharging and venting of the coolant supply, and shutting down during nonuse or upon occurrence of a fault condition.

BRIEF DESCRIPTION OF DRAWINGS

These and other features of the invention will be understood by reference to the description below, read in light of the prior art together with illustrative figures, wherein.

DETAILED DESCRIPTION OF INVENTION

Figure 1:
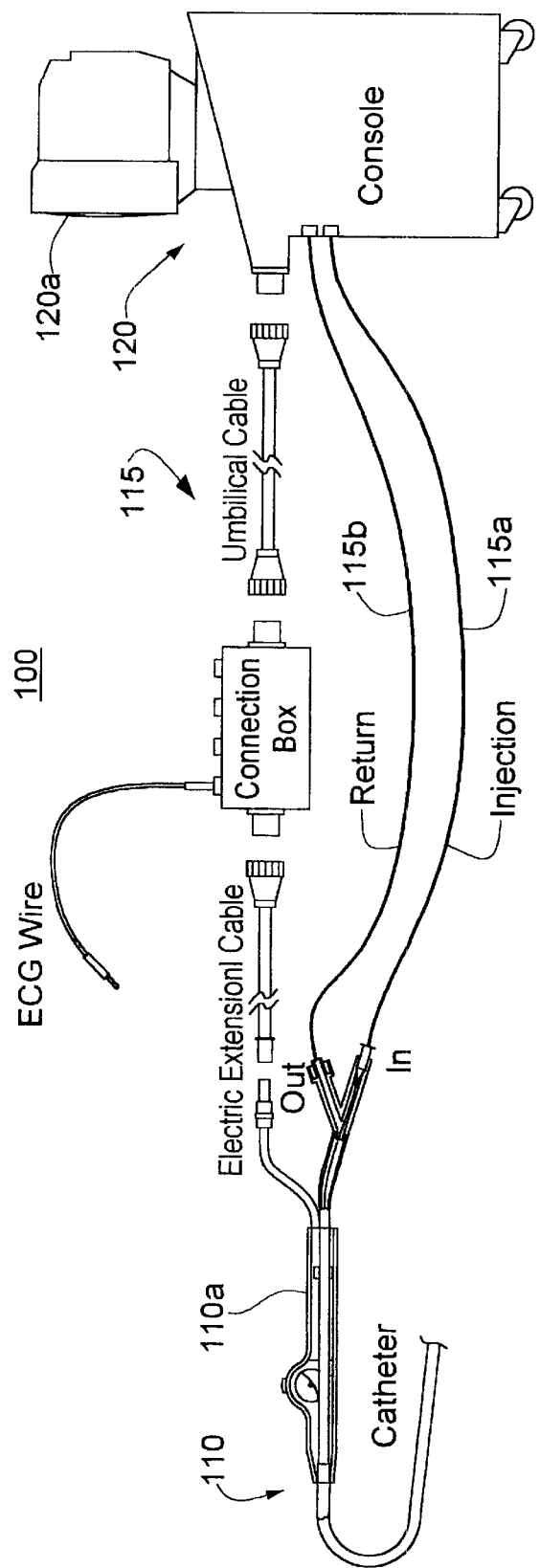
FIGS. 1 and 1A illustrate a cryocatheter treatment system and cryocatheter.

FIG. 1 shows a cryogenic treatment system 100 illustrating the general elements thereof. System 100 includes a treatment catheter 110 having a handle 110a, a treatment console 120 and number of connecting lines 115 which include signal lines for any cardiac monitoring or mapping functions as well as a coolant injection line 115a and a coolant return line 115b. As illustrated, the console includes a display screen 120a which may, for example, show both cardiac electrical signals and various status and control screens related to setting or reporting the cooling functions of the catheter or the ablation regimens being administered therewith.

Figure 1A:
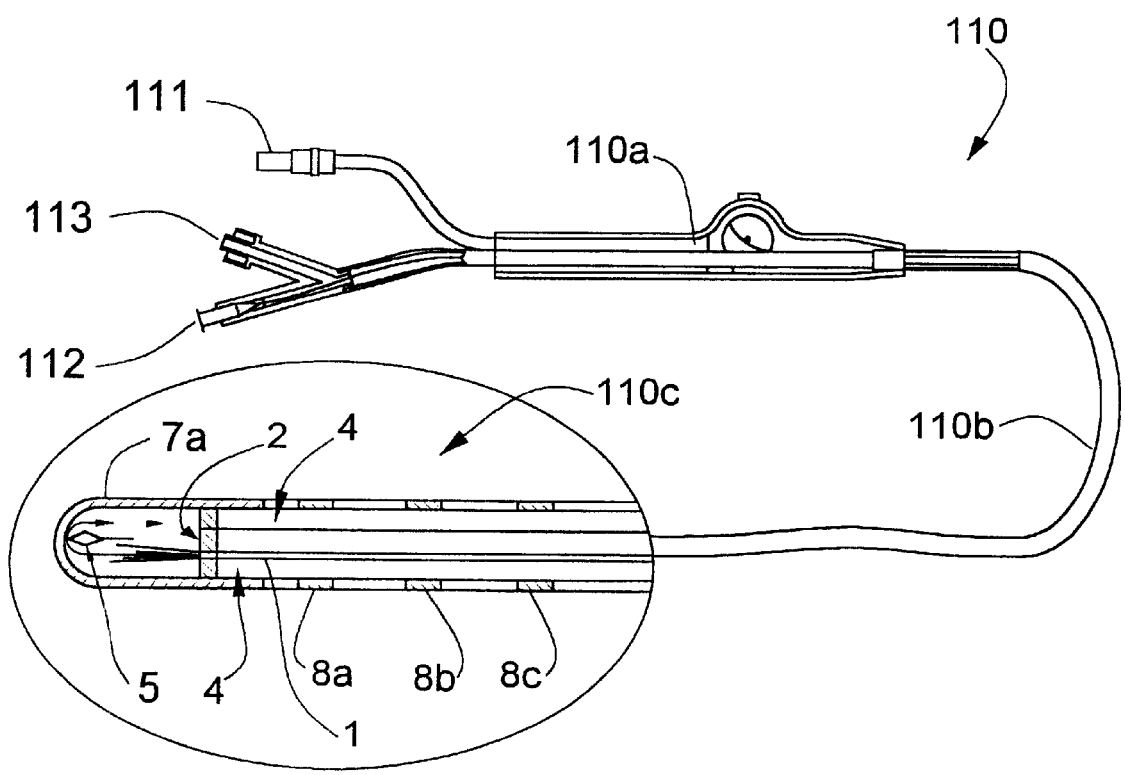

FIG. 1A shows in slightly greater detail a catheter 110 used in a system in accordance with the present invention. As shown, the handle 110a is equipped with input ports for an electrical connector 111, a coolant injection tube connector 112, and a return tube connector 113. These connect via various internal junctions or tubes passing through the handle to provide these three functions to the distal tip of the catheter. The handle may also include various control assemblies, e.g., switches or valves, as well as safety detection or shut down elements (not illustrated).

Leading from the handle 110a is an elongated catheter body 110b which extends to the catheter tip 10c, illustrated in enlarged detail to show a representative structure thereof. As shown, in catheter tip 110c the coolant enters through a central tube 1 and exits via a nozzle 2 at the end of the tube to expand in a small contained region forming a chamber 3 at the tip of the catheter. In the illustrated construction, the tube 1 runs concentrically within an outer tube (not numbered) thereby forming an annular return space 4 surrounding the supply tube 1 and extending back to the fluid return connector 113 of the handle. As discussed further below, the return passage for expended coolant is a vacuum passage, thus assuring that leakage into the blood stream cannot occur.

The location of chamber 3 defines the cooling region of the catheter tip. In the illustrated embodiment this is a short chamber less than a centimeter long located at the very tip of the catheter. Also shown are a thermocouple 5 positioned within the tip to sense tip temperature, and a plurality of electrodes including a tip electrode 7a and one or more ring electrodes 8a, 8b . . . which are positioned near the tip for use in mapping and/or detecting cardiac signals. In other embodiments, the chamber 3 defined at the tip of the catheter may be an elongated chamber several centimeters in length for defining a coolant chamber effective to form linear lesions when placed in contact with tissue such as the cardiac wall. For the linear embodiment, multiple expansion nozzles, a perforated inlet tube end segment, or other variation in the construction of the coolant supply line may be used to assure a high rate of cooling along the full length of the expansion chamber. Furthermore, the chamber wall may be very thin, or formed with a metal sleeve or cap to achieve high heat transfer rates. Other structures within the catheter may include torque or steering wires, or other elements conventional in the art for navigation of the catheter past branch points in vessels, and for urging the catheter tip into contact with a wall once its position is confirmed.

As will be understood from the above, the task of the console is to provide coolant at the tip region in sufficient quantity and for times effective to create the desired lesions. The nature and depth of the lesions created will depend on a number of factors, including the temperature attained in the adjacent tissue, as well as the nature of the cooling cycle by which that temperature is attained. In general when the tissue attains an extremely low temperature, or a temperature effective to create ice crystals within tissue cells, the tissue damage will be irreversible, resulting in effective ablation at the contacted site. The actual cooling rates achieved at the tip will depend to a large extent on the area of contact with the tissue as well as the conductive properties of the adjacent tissue and the structure and geometry of the catheter in addition to the nature of coolant flow passing through the catheter tip. In the present system applicant controls the latter quantity, as discussed more fully below, by providing a controller in which the flow of a phase change coolant supplied to the tip is varied to directly control the amount of cooling power available during an ablation cycle. In addition, the primary cooling effect is achieved by expansion of coolant at the inlet nozzle 2 as it enters chamber 3.

While not illustrated, one or more electrical sensing elements in addition to the thermocouple may be provided at various places within the catheter to provide useful feedback or emergency control functions. For purposes of the present patent application, such functions will not be further discussed. However, if provided they may be positioned in a discrete cooling system, which for purposes of illustration may be considered to lie entirely within the console 120, or be external thereto, but in any case to function in relation to the coolant supply elements which will now be described below.

Figure 2:
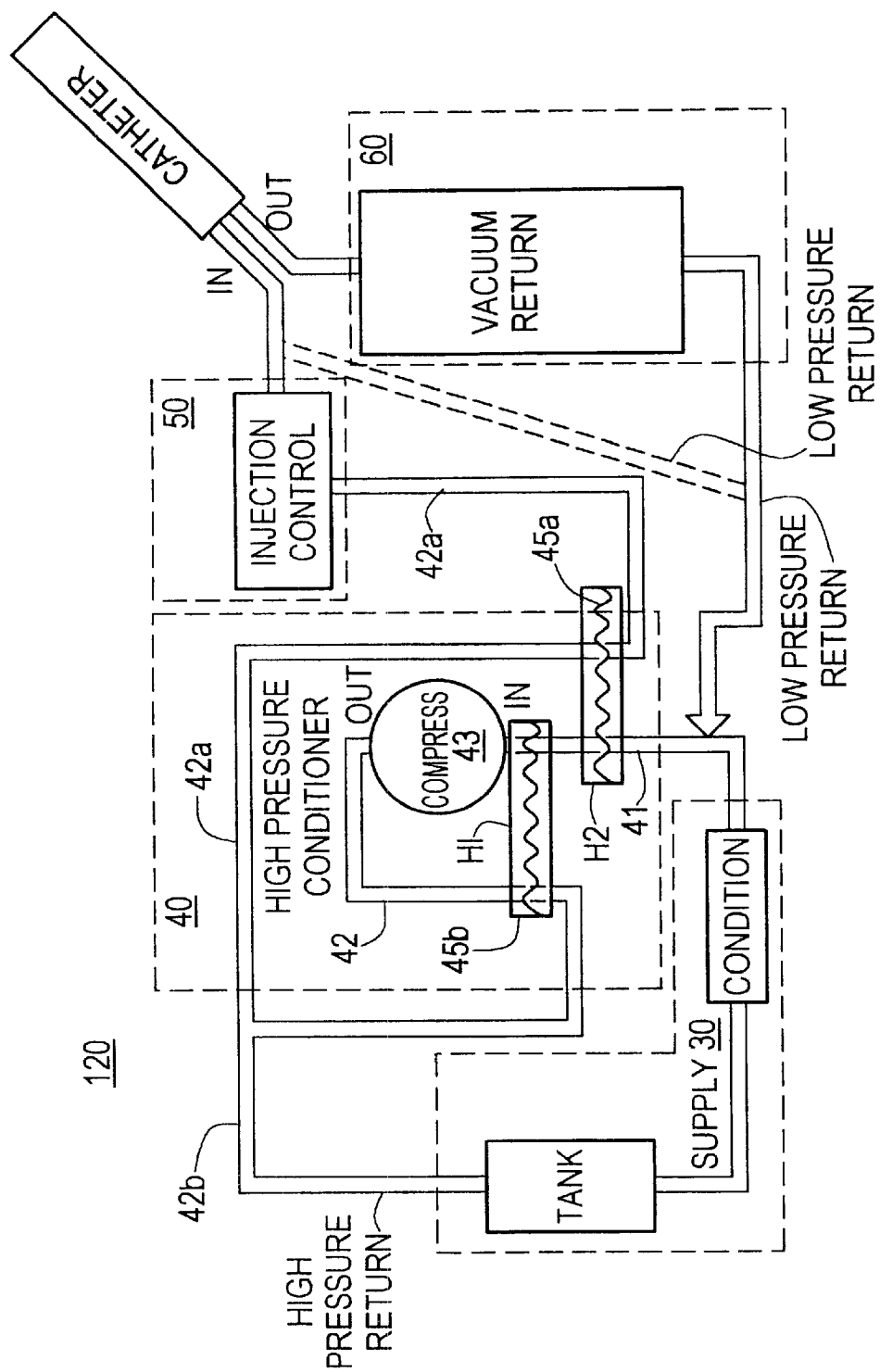
FIG. 2 is a schematic representation of a coolant system in accordance with one embodiment of the present invention for use with the catheter of FIG. 1.

FIG. 2 illustrates one embodiment of a cooling system in accordance with the present invention configured to connect to the inlet and return ports 112, 113 of the catheter 110 (FIG. 1A). As shown, the coolant system 120 includes a coolant supply 30, a coolant conditioner 40, a coolant control 50 and a coolant return section 60. The control section 50 connects to the inlet 112 of the injection catheter, for example by a supply tube, while the return system 60 connects to coolant return port 113. These are illustrated as separate connections, but as discussed more fully below, they may be implemented with a single vacuum-jacketed line with a quick connect coupler, or other specialized connection which allows a single coupling to the catheter handle for all coolant functions. Similarly, electrical connections may be incorporated in such a single conduit, or may be provided as separate signal cabling. Operation of the coolant system 120 will be most fully understood from a detailed discussion of each of the subassemblies 30, 40, 50, 60.

In general terms, the coolant system has a coolant conditioning section 40 with a compressor that provides a conditioned phase change coolant at elevated pressure to the control section 50, which, in turn, regulates the supply of coolant provided to the inlet of the catheter. The return section 60 includes a vacuum pump which continuously draws expended coolant from the catheter at lower pressure and returns it at higher pressure to the coolant conditioner 40, thereby providing a closed circulation loop through the catheter to meet the required ablation or mapping regimens. In the preferred embodiment, the conditioner provides coolant substantially at ambient temperature or colder, and the controller includes an electronically controlled pressure regulator which sets the flow rate of the coolant injected into the catheter, thus regulating the cooling action of the catheter tip. Conditioned coolant is provided to the control section by the conditioner 40, which receives coolant at lower pressure either from the return section 60 or from the supply 30, compresses the coolant to a high pressure, liquefies the coolant, and brings it to approximately ambient temperature at its outlet line 42a leading to the controller. As further shown in FIG. 2, the output from the compressor has a second branch 42b in which excess coolant is not further cooled, but is simply returned to the supply 30.

As noted above, conditioner section 40 in addition to the raising the pressure of the coolant supplied to the regulator for controlled injection into the catheter, also conditions the temperature of the high pressure coolant. This is preferably done as shown in FIG. 2, by heat exchange between the inlet supply line 41 and the compressor outlet line 42. As shown in the Figure, the compressor outlet line 42 is placed in heat exchange communication, for example via a condenser or heat exchanger 45b, with the inlet line 41. In addition one output branch 42a of the outlet line 42 is placed in heat exchange communication, for example via exchanger 45a, with an upstream portion of the inlet line 41. The compressor 43 operates to compress the coolant from a relatively low pressure, preferably below several atmospheres, to a considerably higher pressure, e.g., 20 to 30 atmospheres as measured in its outlet line 42. The material in line 42 is therefore heated by compression, and the heat exchange with inlet line 41 serves to reduce the temperature rise generated by compression. Furthermore, by providing only a portion of compressor output, namely the catheter-directed branch 42a to the upstream, colder portion of the compressor inlet line 41, the catheter injection supply of coolant is effectively brought to or near ambient temperature or colder, while the downstream heat exchange effected in heat exchanger 45b with the entire output of the compressor is cooled to a lesser extent, serving a more traditional function of liquefying the coolant output and enhancing the overall cooling capacity of the compressed fluid. This ordered heat exchange arrangement provides preferentially greater cooling to the catheter-directed supply line, resulting in a stabilized catheter input over a broader range of operating cycles.

In FIG. 2 the high pressure return 42b to the tank may be implemented with a pressure regulator located in-line ahead of the tank inlet to assure that coolant is returned to the tank only when its use elsewhere in the circulation loop is not required, and that the pressure in the line first builds up to a level higher than the current tank pressure.

Thus the system of the present invention provides a closed loop coolant circulation system wherein coolant is conditioned for provision to the inlet of a control module which injects the coolant into a catheter, and the coolant returns in a closed loop to provide a continuous circulation of fluid at ambient temperature or colder into the catheter.

Figure 3:
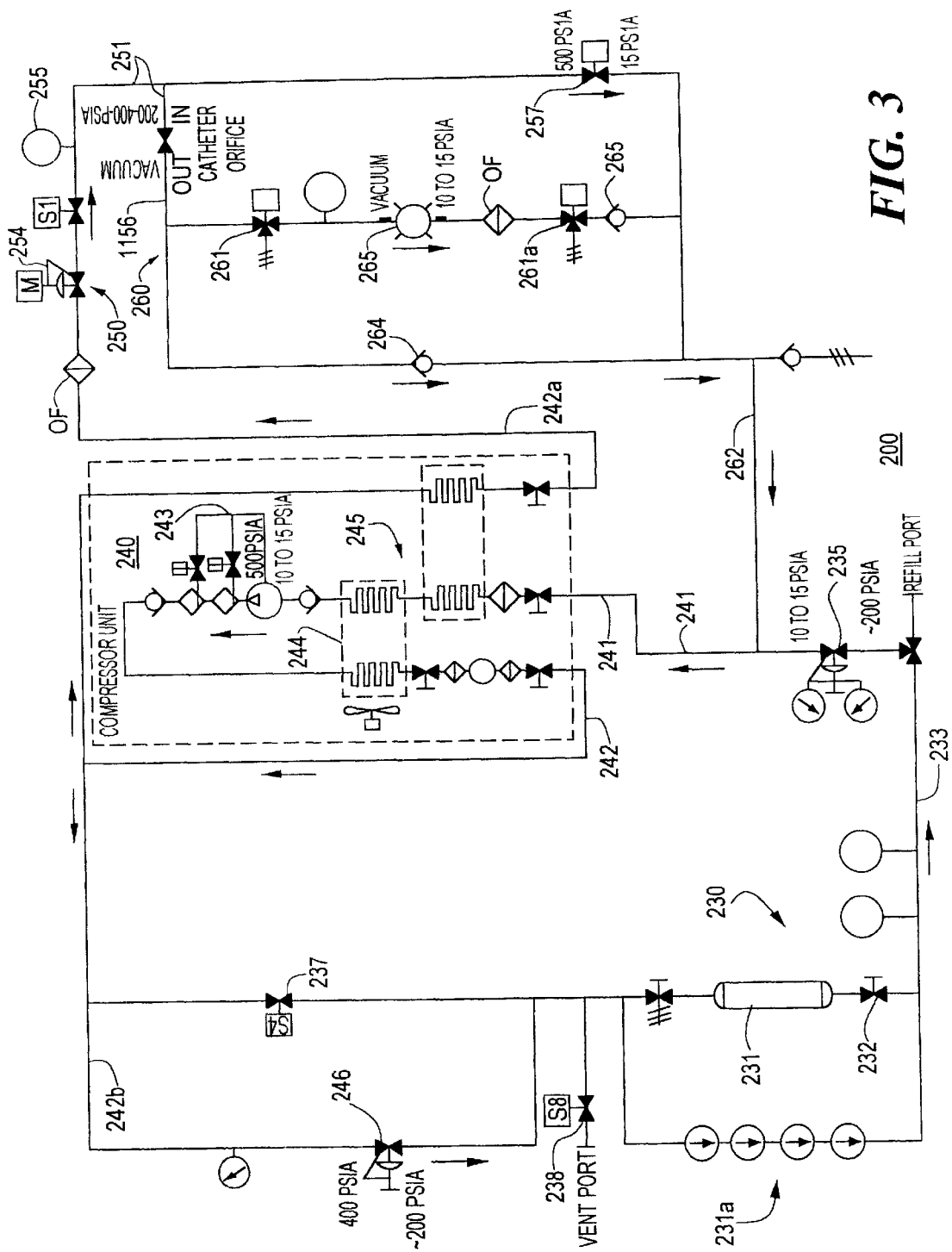
FIG. 3 is a detailed schematic of another implementation of the coolant system of the present invention.

FIG. 3 shows a prototype embodiment in greater detail, illustrating representative valves and regulators for implementing a preferred closed loop coolant supply 200. The coolant supply, compressor, control and return portions of system 200 are numbered with numerals 230, 240, 250, and 260 corresponding to the related subassemblies 30, 40, 50 and 60 of system 20. As shown in this embodiment, a refrigerant tank 231 equipped with a magnetic sight glass 231a to indicate fill level, supplies refrigerant through a needle valve 232 along line 233 to a downstream pressure regulator 235. The pressure regulator 235 converts the nominal tank pressure of several hundred pounds per square inch to a fixed level of 14 psia to provide a constant supply pressure to the inlet line 241 of the compressor. At this stage the refrigerant is boiling at a temperature of about −60° Fahrenheit. The vacuum recovery return line 262 joins the refrigerant inlet 241 at this point.

The compressor inlet line 241 passes through heat exchanger 245 en route to the compressor 243, and also passes through a condenser 244, so the low pressure liquid in the inlet line 241 is heated by the hot vapor coming out of the compressor, causing it to become a vapor. The compressor 243 takes the vapor and pressurizes it to about 400 psi. The pressurized output passes along line 242 through dryers D and sight glass SG, after which the high pressure outlet line bifurcates into two branches 242b and 242a. An upstream pressure regulator 246 in line 242b builds and maintains pressure in the high pressure output line allowing the regulator to open and return excess refrigerant to the tank 231 when the pressure reaches a preset level, of about 400 psi, which is higher than the nominal tank pressure, e.g., 200 psi.

The second branch 242a of the output line 242 passes through the heat exchanger 245 located in the upstream portion of the input line 241, where it is further cooled to provide a conditioned output to the controller 250, which as shown includes a motorized pressure regulator 254. Pressure regulator 254 controls the flow rate of coolant provided along line 251 to the inlet port of the catheter (illustrated schematically). By way of example, the pressure regulator 254 may be controlled by a control microprocessor in the console to provide coolant at a pressure of 250 psi for a time interval of 2.5 minutes. Control is generally done by actuating the motor of regulator 254 to achieve a desired set point and leaving the regulator at that setting for the indicated time period. A zero to 500 psi pressure transducer 255 is placed in line 251 to provide feedback signals for implementing the control of the regulator 254, which may further employ feedback from the thermocouple in the catheter.

The foregoing values of pressure and duration are given by way of example only, and it will be understood that typical cooling regimens implemented by the control console 120 (FIG. 1) may run from several seconds to five minutes or more, and that the coolant pressures which are varied to achieve a desired rate of heat transfer or effective lesion depth may vary from the coolant pressure in the tank to approximately the pressure of the compressor output line 242a. Advantageously, the pressure in line 251 remains greater than the saturation pressure of the refrigerant being used such that it does not start to boil before it reaches the tip.

As further shown in FIG. 3, the return line 115b from the catheter attaches to vacuum section 260, while a solenoid operated purge valve 257 extends between the catheter inlet line 251 and the low pressure return line 262 from the vacuum scavenging system 260. It will be understood that purge valve 257 will typically be operated to bleed the inlet line when the catheter is first attached and the supply compressor or return pump, respectively, are operated.

The return line 115b from the catheter passes via vacuum protection solenoid-operated valve 261 to a vacuum pump 265, which maintains a vacuum in the range of 2 to 40 millibars in the return line, and which increases the pressure of the expended coolant vapor to approximately 15 psi. At the outlet side of the vacuum pump a similar solenoid operated protection valve 261a is provided together with a check ball, and an oil filter OF which prevents pump oil from contaminating the circulating coolant or depositing in the coolant valves, catheter passages or other components. A filter, e.g., 0.5 μm, appears in the catheter inlet line 251. The entire vacuum system may be isolated by the solenoid operated protection valves 261, 261a, during start-up or during a sensed over-pressure or blood leakage condition, and a check valve 265 prevents any pressure build-up on the vacuum pressure side of the catheter in the event of pump or compressor failure, allowing coolant return directly into the return line 262 and compressor inlet 241. For this purpose, the compressor output or various bypass or check valves 257, 264 are set a pressure slightly higher than the output setting of the tank conditioner regulator 235, so that the coolant normally circulates into the catheter and through the vacuum system back into the compressor as a closed loop.

In the illustrated embodiment, a coolant refill port 275 is provided at a solenoid operated valve 277 in the compressor inlet line 241, allowing a refrigerant bottle attached at that point to employ the same compressor 243 of the system to refill the supply tank 231. For this purpose, a solenoid operated by-pass valve 237 is also supplied to bypass the upstream high pressure return regulator 246 between the compressor output line 242b and the tank, and speed up refill of the tank 231. Preferably, above the tank, a solenoid operated valve 238 connects to a vent port to allow venting of any air which may have accumulated in the refrigerant tank due to leakage through the catheter or tubing. This vent is preferably controlled automatically by a suitable control program in the console 120. Venting may be implemented, for example, by providing a temperature sensor in the refrigerant tank and a pressure sensor at its top. Knowing the temperature of the liquid refrigerant in the tank, the vent may be operated until the saturated pressure is reached for the given refrigerant at the indicated tank temperature. Such a venting step is to be performed each time the console is turned on. In addition to the foregoing elements, various pressure indicators or temperature sensors may be situated along the different lines to indicate operating parameters of the fluid therein. These are preferably sensors or indicators of the process control type wherein, rather than a dial display output, they provide an electrical output which connects to a microprocessor programmed to monitor the various conditions continuously to detect relevant safety, control or maintenance conditions.

The invention being thus disclosed and described in illustrative embodiments herein, variations and modifications as well as adaptations of the invention to other systems will occur to those skilled in the art, and all such variations, modifications and adaptations are considered to lie within the scope of the invention as described herein and defined in the claims appended hereto and equivalents thereof.

What is claimed is:

1. A coolant system for providing cryoablation fluid to a cryotreatment probe such as a mapping or ablation catheter, wherein the coolant system comprises
    a tank for holding a coolant liquid, said tank having an inlet and an outlet
    a pressure regulator for reducing pressure of liquid from the outlet for facilitating phase change of said liquid
    a heat exchanger for placing a catheter coolant injection line in heat exchange relation with said reduced pressure liquid to thereby cool the coolant injection line
    a compressor, and a condenser, the reduced pressure liquid passing through the condenser and into the compressor to form a hot pressurized vapor output
    the hot pressurized vapor output passing through the condenser along said injection line to become a cooled pressurized output while vaporizing the reduced pressure liquid prior to its entry into the compressor, and
    pressure regulation means downstream of the condenser,
    said pressure regulation means
        building up pressure of said cooled pressurized output in a first branch for returning coolant to the tank inlet, and
        conditioning and controlling the coolant in a second branch for injection into the cryotreatment probe.

2. The coolant system of claim 1, further comprising
    a vacuum recovery unit connectable to the probe for receiving return flow of injected coolant therefrom
    said vacuum recovery unit including a vacuum pump which receives said return flow at a vacuum inlet side thereof and pumps it to a pump outlet side, and
    a recovery return line extending from said pump outlet side to the reduced pressure liquid downstream from the tank outlet thereby forming together with the catheter a supply loop for said cryoablation fluid.

3. The coolant system of claim 2, further comprising a bypass return line connected between said probe inlet side and said recovery return line, said bypass return line including a pressure regulator for reducing pressure from said probe inlet side to a lower pressure of said recovery return line, and wherein said lower pressure of the recovery return line is higher than pressure of the reduced pressure liquid from the refrigerant tank, thereby assuring circulation of cryoablation fluid in the supply loop through the probe, the compressor and the condenser.

4. A cryoablation system comprising a coolant console having
    a reservoir of phase change coolant
    first means for providing the phase change coolant from the reservoir at elevated pressure along an inlet line to a cryotreatment probe
    second means for recovering the phase change coolant from the cryotreatment probe and raising its pressure
    said first and second means forming a supply loop through the cryotreatment probe and the first means being arranged in heat exchange communication to condition the coolant before it reaches the probe along the inlet line so as to achieve effective cooling regimens by controlling phase change coolant provided along the inlet line while continuously recovering and recirculating expended coolant, wherein the second means includes a vacuum pump configured to draw expended coolant from the cryotreatment probe, and said vacuum pump raises pressure of said expended coolant for return to the first means.

5. The cryoablation system of claim 4, wherein the reservoir provides said phase change coolant at a first pressure to said first means, and the vacuum pump returns the expended coolant to the first means along a return line at a pressure above said first pressure.

6. A coolant system for operation of a cryotreatment catheter to treat a patient, such system comprising a reservoir of phase change fluid a compressor for elevating the pressure of said fluid a conditioning assembly for conditioning temperature of the elevated pressure fluid a microprocessor-controlled pressure regulator for setting a cryotreatment supply regimen of defined pressure and duration to supply an effective amount of conditioned fluid to a coolant port of the cryoteatment probe, and a vacuum recovery assembly connectable to the cryotreatment probe for continuously drawing expended fluid from the probe thereby preventing leakage into the bloodstream of the patient, wherein the vacuum recovery assembly returns the expended fluid at intermediate pressure to the compressor thereby forming a closed supply loop of said conditioned temperature elevated pressure fluid supplied to the pressure regulator, wherein the intermediate pressure is less than the pressure of the fluid from the compressor and greater than the pressure of the expended fluid.

* * * * *